(12) United States Patent
Cordato

(10) Patent No.: US 7,033,170 B2
(45) Date of Patent: Apr. 25, 2006

(54) ORTHODONTIC BRACKET AND CLIP

(76) Inventor: Mark Andrew Cordato, P.O. Box 1298, Bathurst, New South Wales (AU) 2795

( * ) Notice: Subject to any disclaimer, the term of this patent is extended or adjusted under 35 U.S.C. 154(b) by 0 days.

(21) Appl. No.: 10/842,948

(22) Filed: May 11, 2004

(65) Prior Publication Data
US 2005/0255422 A1    Nov. 17, 2005

(51) Int. Cl.
*A61C 3/00*    (2006.01)
(52) U.S. Cl. ............................ 433/10; 433/8
(58) Field of Classification Search .............. 433/8–15, 433/17
See application file for complete search history.

(56) References Cited

U.S. PATENT DOCUMENTS

| | | | |
|---|---|---|---|
| 2,019,773 A | 11/1935 | Wirt | |
| 2,671,964 A | 3/1954 | Russell et al. | |
| 3,091,857 A | 6/1963 | Rubin et al. | |
| 3,128,552 A * | 4/1964 | Broussard | 433/13 |
| 3,391,461 A | 7/1968 | Johnson | |
| 3,438,132 A | 4/1969 | Rubin | |
| 3,597,845 A * | 8/1971 | Russ | 433/17 |
| 3,772,787 A | 11/1973 | Hanson | |
| 3,780,437 A | 12/1973 | Wildman | |
| 3,854,207 A | 12/1974 | Wildman | |
| 3,975,824 A | 8/1976 | Lee | |
| 4,161,066 A | 7/1979 | Morrow et al. | |
| 4,192,070 A | 3/1980 | Lemchen et al. | |
| 4,209,906 A | 7/1980 | Fujita | |
| 4,268,249 A | 5/1981 | Forster | |
| 4,302,532 A | 11/1981 | Wallshein | |
| 4,355,975 A | 10/1982 | Fujita | |
| 4,427,381 A | 1/1984 | Hall | |
| 4,492,573 A | 1/1985 | Hanson | |
| 4,551,094 A | 11/1985 | Kesling | |
| 4,838,787 A | 6/1989 | Lerner | |
| 5,094,614 A | 3/1992 | Wildman | |
| 5,123,838 A | 6/1992 | Cannon | |
| 5,129,821 A | 7/1992 | Schuetz | |
| 5,160,261 A | 11/1992 | Peterson | |
| 5,224,858 A | 7/1993 | Hanson | |
| 5,248,257 A | 9/1993 | Cannon | |
| 5,275,557 A * | 1/1994 | Damon | 433/10 |
| 5,322,435 A | 6/1994 | Pletcher | |
| 5,356,288 A | 10/1994 | Cohen | |
| 5,380,197 A | 1/1995 | Hanson | |
| 5,429,500 A * | 7/1995 | Damon | 433/10 |
| 5,474,445 A | 12/1995 | Voudouris | |
| 5,516,284 A | 5/1996 | Wildman | |
| 5,540,586 A | 7/1996 | Hanson | |

(Continued)

FOREIGN PATENT DOCUMENTS

WO    WO 02/065939 A1    8/2002

*Primary Examiner*—Kevin Shaver
*Assistant Examiner*—Patrick J. Kilkenny
(74) *Attorney, Agent, or Firm*—Dorr, Carson, Birney, P.C.

(57) ABSTRACT

An orthodontic bracket assembly has a bracket having base with a mounting portion for attachment to a patient's tooth, and a plurality of arms forming a bracket slot to receive a rectangular archwire. A clip can be removably inserted into the bracket slot along the axis of the bracket slot and archwire, and is retained by the bracket slot. The assembled bracket slot and clip form a rectangular channel to removably secure the archwire in the bracket slot. Two of the archwire surfaces are engaged by the clip and the remaining two archwire surfaces are engaged by walls of the bracket slot.

18 Claims, 7 Drawing Sheets

U.S. PATENT DOCUMENTS

| | | |
|---|---|---|
| 5,562,444 A | 10/1996 | Heiser et al. |
| 5,586,882 A | 12/1996 | Hanson |
| 5,618,176 A | 4/1997 | Andreiko et al. |
| 5,630,715 A * | 5/1997 | Voudouris .................... 433/8 |
| 5,711,666 A | 1/1998 | Hanson |
| 5,738,513 A | 4/1998 | Hermann |
| 5,762,492 A | 6/1998 | Kanomi et al. |
| 5,890,893 A | 4/1999 | Heiser |
| 5,913,680 A | 6/1999 | Voudouris |
| 5,971,753 A | 10/1999 | Heiser |
| 6,042,373 A | 3/2000 | Hermann |
| 6,071,119 A | 6/2000 | Christoff et al. |
| 6,095,808 A | 8/2000 | Nakagawa |
| 6,142,775 A | 11/2000 | Hansen et al. |
| 6,168,429 B1 * | 1/2001 | Brown ........................ 433/11 |
| 6,264,469 B1 | 7/2001 | Moschik |
| 6,302,688 B1 * | 10/2001 | Jordan et al. .................. 433/8 |
| 6,347,939 B1 | 2/2002 | Abels |
| 6,506,049 B1 | 1/2003 | Hanson |
| 6,655,957 B1 * | 12/2003 | Abels et al. .................. 433/10 |
| 6,663,385 B1 * | 12/2003 | Tepper ........................ 433/11 |
| 6,695,612 B1 * | 2/2004 | Abels et al. .................. 433/10 |
| 6,733,286 B1 * | 5/2004 | Abels et al. .................. 433/11 |
| 6,866,505 B1 * | 3/2005 | Senini ........................ 433/10 |
| 2001/0005574 A1 | 6/2001 | Manemann et al. |
| 2002/0119414 A1 | 8/2002 | Orikasa |
| 2003/0039938 A1 | 2/2003 | Orikasa |

* cited by examiner

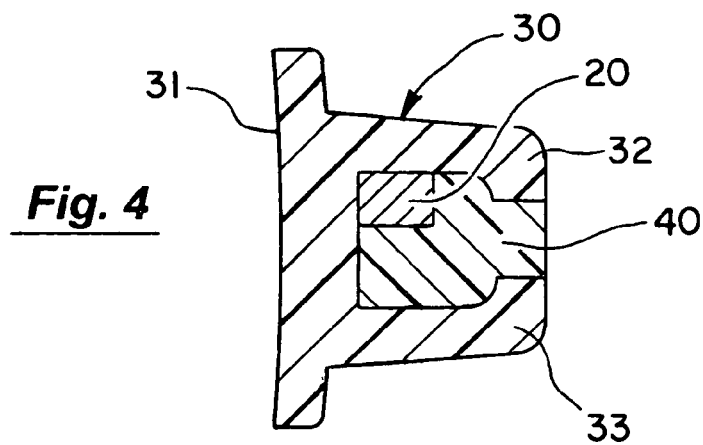
*Fig. 4*
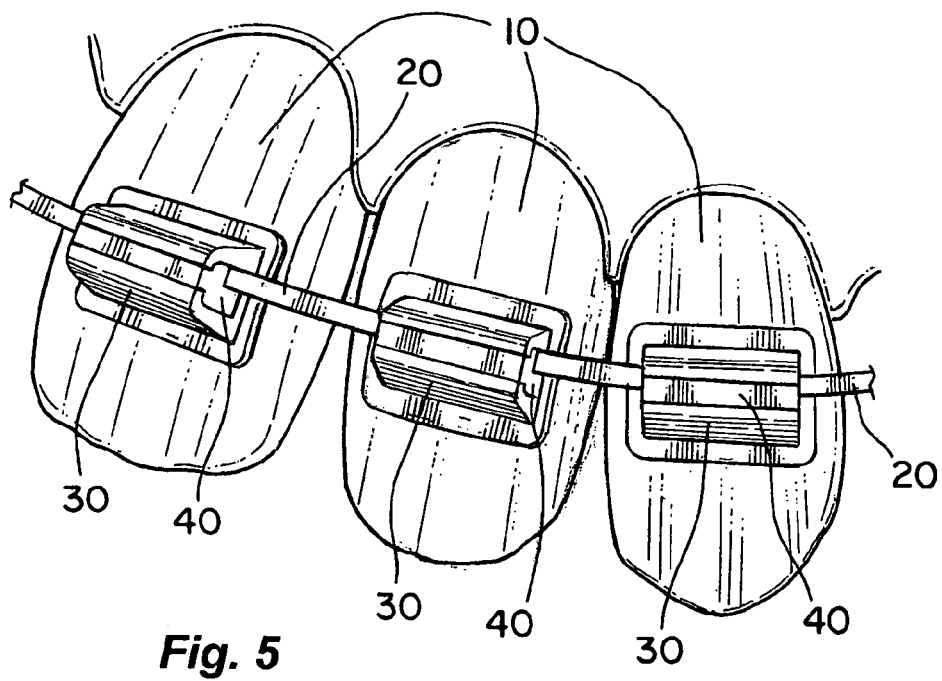
*Fig. 5*
*Fig. 6*
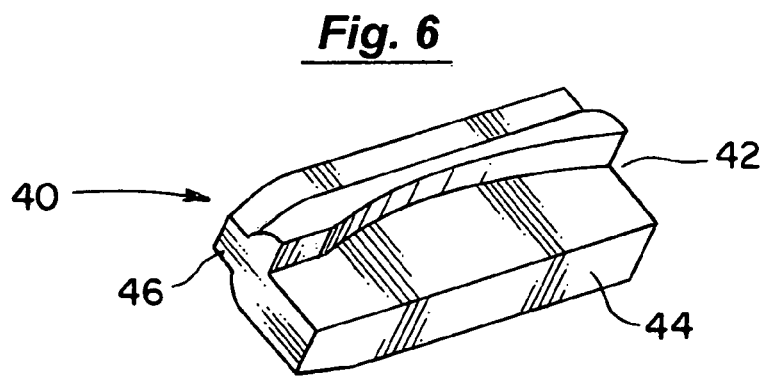

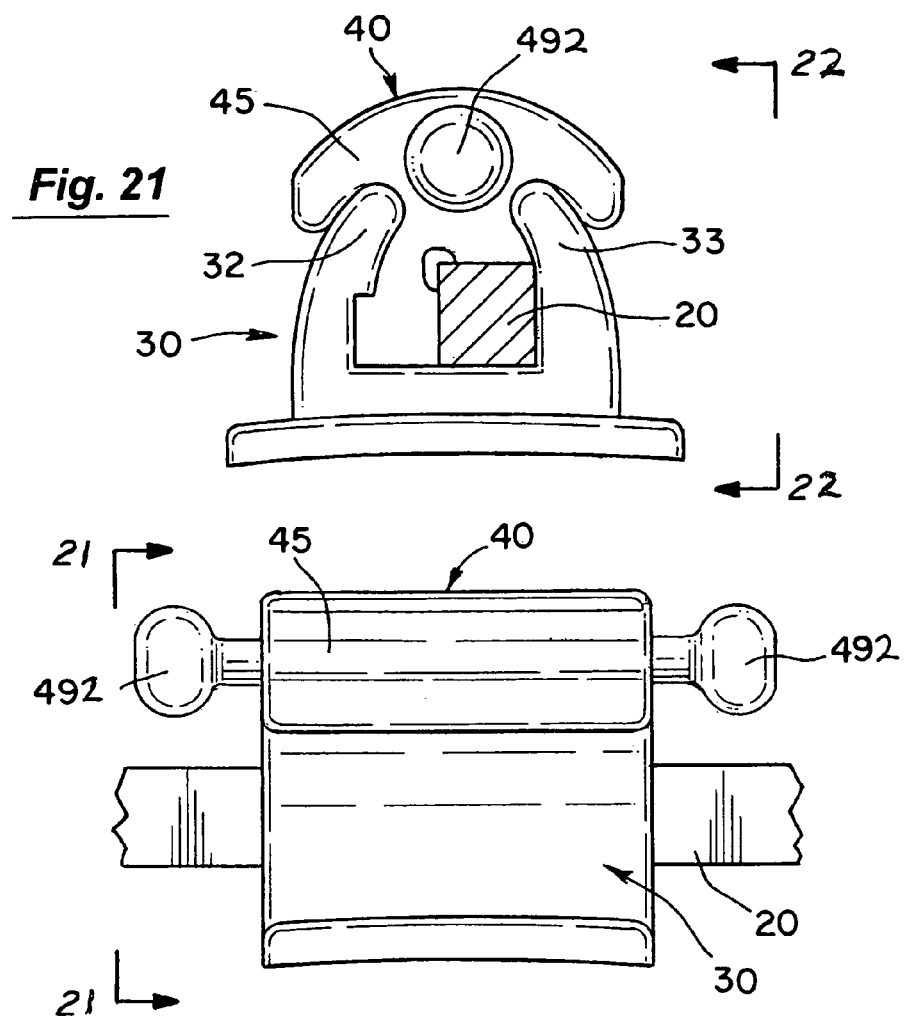
Fig. 21
Fig. 22
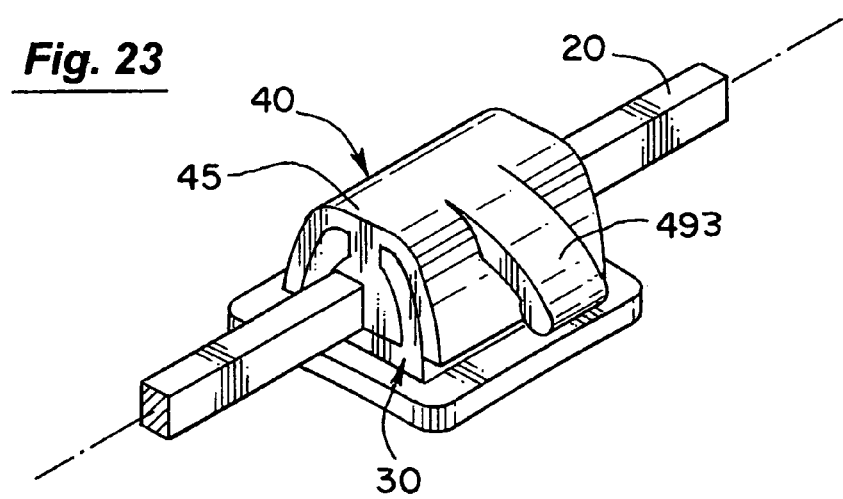
Fig. 23

ORTHODONTIC BRACKET AND CLIP

BACKGROUND OF THE INVENTION

1. Field of the Invention

The present invention relates generally to the field of orthodontic devices and methods for maintaining an orthodontic archwire relative to a tooth. More specifically, the present invention discloses an orthodontic bracket with a removable clip that can be inserted into the bracket slot of the bracket along the axis of an archwire to secure the archwire to the bracket.

2. Statement of the Problem

In the field of orthodontics and orthodontic armamentarium, the orthodontic bracket is a central component of current, orthodontic practice. Orthodontic brackets were first developed by Dr. Edward Hartley Angle in the late 1800's and in spite of significant improvements in design, materials and manufacturing processes that have occurred since Dr. Angle's time, the biomechanical functioning of orthodontic brackets remains essentially unchanged.

The primary functional feature of conventional orthodontic brackets is the archwire slot. The archwire slot is a generally horizontally oriented, outwardly opening, rectangular-in-cross-section trough formed in the structure of a bracket intended to accept a separate, round, square or correspondingly rectangular-shaped archwire. A refinement of the orthodontic bracket developed by Dr. Angle is known as the "edgewise"-type bracket. The term "edgewise" is a descriptive term referring to the rectangular inter-fit of the archwire slot and the rectangular archwires typically employed for edgewise orthodontic therapy. The rectangular inter-fit of the archwire in the bracket's slot enables full conveyance of corrective energy stored in a deflected archwire to be transmitted to the tooth, the root and into the bony support structure of a patient's jaws.

The archwire slot of conventional orthodontic brackets consists of an archwire slot floor and two archwire slot walls. The walls are parallel to each other and are in turn generally parallel to the occlusal plane. The floor of the slot is oriented perpendicular to the walls thus forming two 90° corners extending along the floor. Such an archwire slot is considered as being an "open" slot because an archwire can drop into it from the labial or buccal directions due to the slot having no fourth side.

Within the field of orthodontics, dimensional standards have been established for the dimensions of archwire slots. For example, the standard dimensions of 0.018 and 0.022 inches relate the slot width, plus an allowance for manufacturing tolerances. These values are known as "slot size". The depth of the slot may be 0.025 in. for a slot that is 0.018 in. wide, and 0.028 in. for a slot that is 0.022 in. wide. Brackets with the standard 0.018×0.025 in. and 0.022×0.028 in. archwire slot dimensions are available to orthodontists from many commercial sources.

Even though Dr. Angle's bracket design has become the standard and is utilized widely, edgewise brackets still have limitations and shortcomings in use. For example, at a later stage of treatment orthodontists will typically attempt to insert what is known as a full-size or finishing archwire into the archwire slots of a patient's brackets. Such archwires are generally very stiff, having a tensile strength of up to 310 KSI UTS and a modulus of elasticity approaching 30,000,000. The term "full size" relates to an archwire that is manufactured to rectangular dimensions that fully fill a bracket's archwire slot thus taking full advantage of the edgewise philosophy. In such a relationship, the walls and floor of the archwire slot will be in intimate, coplanar contact with the outer surfaces of such an archwire. It must be understood that the stage of treatment where an orthodontist would first attempt to insert a full-size finishing archwire coincides with the patient's teeth having been only partially repositioned toward their ideal finished positions. The patient's teeth at such a stage lack final aesthetic and gnathologic positioning required for a stable occlusion and a good finished result. Because of this, the various bracket archwire slots will fall somewhat out of alignment relative to each other just as the teeth they are attached to are. Due to the difficulty associated with attempting to insert a very stiff and tightly-fitting archwire into various unaligned archwire slots, an orthodontist must often times use instruments known as torqueing wrenches to distort the archwire locally at each bracket/archwire interface. The wrenches are used to bend and orient the archwire so that it can drop into its corresponding bracket's archwire slot. For the next adjacent bracket the archwire must again be distorted to conform to the orientation of its archwire slot. Such distortion then is biased against the previous bracket's orientation and will in turn be biased relative to the subsequent bracket's orientation, and this difficult and time consuming process must be repeated all around the patient's arch. As can be appreciated, wrestling a finishing archwire into typically ten archwire slots around the patients upper or lower dental arch is time-consuming for the orthodontist and can be uncomfortable for the patient.

Throughout the foregoing, it should be appreciated that orthodontic treatment is initiated with archwires exhibiting a low spring rate and high deflection, and sequentially superseded with archwires that exhibit progressively higher spring rates at lower deflections. Over the course of treatment the steps of removing and then replacing a series of sequential archwires consumes a significant portion of the total time an orthodontist and staff can devote to a patient's care.

In all cases, once archwires are positioned into the series of archwire slots, the archwire must be then retained in each of the slots. Standard orthodontic brackets have features known as ligation wings or tie wings that are intended to inter-work with a separate ligature device thus creating a means with which to hold archwires fully seated and in place in the brackets.

Ligatures can be formed from urethane elastomers using the injection molding process. Such elastomeric ligatures are configured in the shape of tiny o-rings. Elastomeric ligatures are hooked over one pair of a conventional bracket's tie-wings and then pulled up and over the archwire and hooked over the opposite pair of tie wings. Orthodontic instruments are typically required to accomplish the step of ligation.

Stainless steel ligatures may also be used. Stainless steel ligatures are formed from fully annealed 0.009 inch through 0.012 inch diameter round wire. Steel ligatures are similarly tied around the tie wings of a conventional bracket and over the archwire thus retaining the archwire in its archwire slot. Once tied, the loose ends of the wire are twisted and the excess wire is cut off. The twisted section of the wire is then tucked under the tie wings so as to be out of the way to avoid laceration of the soft tissues of the tongue and cheeks. Similar to ligation using elastomeric ligatures, steel ligatures also require the use of several specialized dental instruments.

From the foregoing, it can be seen that the steps of installing, removing and replacing archwires (particularly full-size finishing archwires) are a time consuming and sometimes challenging task for an orthodontist and staff.

The changing of archwires can also be a painful experience for the patient. The step of ligating archwires into each of the brackets is likewise a time-consuming aspect of orthodontic treatment that requires dedicated instruments and focused attention on a tooth-by-tooth basis.

In addition to the limitations of conventional brackets as described above, the standard configuration of conventional orthodontic brackets creates other problems. For example, occlusally-extending and gingivally-extending tie wings shield the facial surfaces of the teeth from tooth brushing and irrigation creating conditions that are ideal for the growth and protection of oral bacteria. The consistent presence of bacteria under the tie wings of a conventional bracket can lead to decalcification of the enamel adjacent to brackets. The presence of bacteria over time can deplete the oxygen bound up in the passivating surface of stainless steel leading to a potential for corrosion problems of the orthodontic hardware itself.

The spacing of the features of conventional brackets, particularly in an occlusal-gingival axis required to accommodate the tie wings and a central slot requires that a standard bracket be at least 3.2 mm in occlusal-gingival extent. This minimum requirement means that a conventional bracket cannot be less than a set minimum size and therefore conventional brackets are considered by some as unavoidably large. Large brackets can contribute to soft tissue irritation and patient discomfort, which can then impact a patient's attitude and loss of the important willingness of a patient to cooperate with his or her treatment. Large brackets can also contact teeth on the opposing arch which can cause damage and wear. Orthodontic patients are often self-conscious, and a "metal mouth" appearance associated with the large relative size of conventional orthodontic brackets can be another factor that does not foster a cooperative attitude by the patient.

Efforts have been made in the past to address these shortcomings and limitations associated with conventional edgewise orthodontic brackets. For example, U.S. Pat. No. 5,356,288 (Cohen) discloses a "primary bracket" with a horizontal slot for receiving an archwire, and a "secondary bracket" that attaches to the primary bracket to hold the archwire in place. Cohen discloses embodiments in which the secondary bracket slides axially into the slot in the primary bracket. However, only one surface of the archwire, at most, is engaged by the walls of the primary bracket. The other surfaces of the archwire are either engaged by the walls of the secondary bracket or remain unsupported. This approach has significant shortcomings in terms of strength and rigidity, and also tends to require a larger bracket assembly.

In particular, Cohen's secondary bracket must be oriented in axial alignment with the primary bracket for the two parts to slide together. Now, assume that a tooth is significantly intruded relative to an adjacent tooth. During a typical early stage of treatment, the archwire must zigzag in a significant bend after exiting the bracket on the first tooth to engage the bracket on the adjacent tooth. Since Cohen's secondary bracket constitutes essentially an upside-down three-sided arch slot, with a labial slot floor, and perpendicular to that, parallel occlusal and a gingival walls, the secondary bracket fully captures the archwire and restricts its true position to that of being axially aligned, and contained within the secondary bracket. The secondary bracket must, in turn, be held in precise alignment with the primary bracket even when the secondary bracket is only beginning to be inserted into the primary bracket of Cohen. In such an example, the distal end of the secondary bracket would inherently be located in very close proximity to the mesial edge of the bracket on the adjacent tooth while inserting Cohen's secondary bracket into the bracket on the first tooth. This can result in an impossible configuration where during the step of inserting Cohen's secondary bracket, the archwire is asked to make an immediate and abrupt bend as it exits the distal end of the secondary bracket. Assuming any space exists for the archwire to make such a dramatic bend, such a sharp bend would induce a permanent set in the archwire impairing its ability to deliver corrective forces between the two teeth. Further, the act of inserting Cohen's secondary bracket into the primary bracket could be a painful experience for the patient. Mechanically speaking, the only practical way to utilize Cohen's brackets would be to limit their use to a final finishing stage in which the teeth are closer to ideal alignment, combined with the step of manufacturing Cohen's brackets in extremely narrow mesial-distal widths. Utilizing Cohen's brackets would require an orthodontist to remove all of a patient's conventional brackets and replace them with Cohen's brackets for final finishing treatment. There is no cost or treatment benefit to justify such an unorthodox step, and further, Cohen's brackets have no features that would eliminate the positional errors unavoidably suffered in positioning any type of bracket on a tooth. Brackets that were manufactured sufficiently narrow in a mesial-distal extent to allow Cohen's secondary bracket to be inserted without destroying the archwire would then create excessive inter-bracket distance which would impair the required level of physiologically-effective corrective forces to be delivered to the teeth.

Solution to the Problem. The present invention addresses the shortcomings of the prior art by providing an orthodontic bracket with a removable clip that can be inserted into a bracket slot from the lateral edge of the bracket along the axis of the archwire to secure the archwire to the bracket. Two of the archwire surfaces are engaged by the clip and the remaining two archwire surfaces are engaged by the walls of the bracket slot. This approach allows the shapes of the clips to be tailored to the cross-sectional dimensions of each archwire over the course of treatment to simplify insertion of the archwire and clip into the bracket slot, and more securely hold the archwires in place.

There are additional advantages arising from having two archwire surfaces engaged by the clip and the remaining two archwire surfaces engaged by the bracket. This arrangement captures the archwire in one of the corners (i.e., occlusal or gingival) of the bracket slot adjacent to the base of the bracket. If the bracket slot and clip are symmetrical or when multiple, right/left-hand clips are use, the practitioner can select which slot corner to most advantageously position the archwire by flipping the orientation of a clip or using the correct configuration. This enables the practitioner to bias the archwire occlusally or gingivally for each individual tooth, to thereby facilitate needed intrusions or extrusions of teeth during orthodontic treatment.

In contrast to Cohen, the present invention employs a bracket slot that engages two sides of the archwire, and a clip that engages the other two sides. The clip provides only one wall that selectively contacts either the gingival or occlusal face of the archwire. In the example above with regard to Cohen, a practitioner would select one clip that engages the labial and occlusal side of the archwire. The archwire would then be completely free to naturally zigzag as required to elegantly curve into the lateral bracket. The archwire is free to naturally curve to the bracket on the adjacent tooth irrespective of whether the clip is inserted only partially into the first bracket or completely locked in place.

The present invention also eliminates the need for tie wings and ligatures to hold the archwire in place in the bracket slot. This saves time and effort on the part of the orthodontist, and reduces patient discomfort. The absence of tie wings also reduces the visual impact of the bracket assembly, reduces patient discomfort, and eliminates potential places to harbor bacteria.

SUMMARY OF THE INVENTION

This invention provides an orthodontic bracket assembly having a bracket with a base that includes a mounting portion for attachment to a patient's tooth, and a plurality of arms forming a bracket slot to receive a conventional rectangular archwire. A clip can be removably inserted into the bracket slot along the axis of the bracket slot and archwire, and is retained by the bracket slot. The assembled bracket slot and clip form a rectangular channel to removably secure the archwire in the bracket slot. Two of the archwire surfaces are engaged by the clip and the remaining two archwire surfaces are engaged by walls of the bracket slot. These and other advantages, features, and objects of the present invention will be more readily understood in view of the following detailed description and the drawings.

BRIEF DESCRIPTION OF THE DRAWINGS

The present invention can be more readily understood in conjunction with the accompanying drawings, in which:

FIG. 4 is a cross-sectional view of the assembled bracket 30, archwire 20 and clip 40.

FIG. 5 is a perspective view corresponding to FIG. 1 showing a series of teeth 10 with brackets 30 after the archwire 20 and clips 40 have been inserted.

FIG. 6 is a perspective view of another embodiment of the clip 40 with a curved channel 42 to accommodate curvature in the archwire.

FIG. 21 is an end view of another embodiment of the assembled clip 40 and bracket 30.

FIG. 22 is side elevation view of the assembled clip 40 and bracket 30 shown in FIG. 21.

FIG. 23 is a perspective view of another embodiment of the assembled clip 40 and bracket 30.

DETAILED DESCRIPTION OF THE INVENTION

Figure 1:
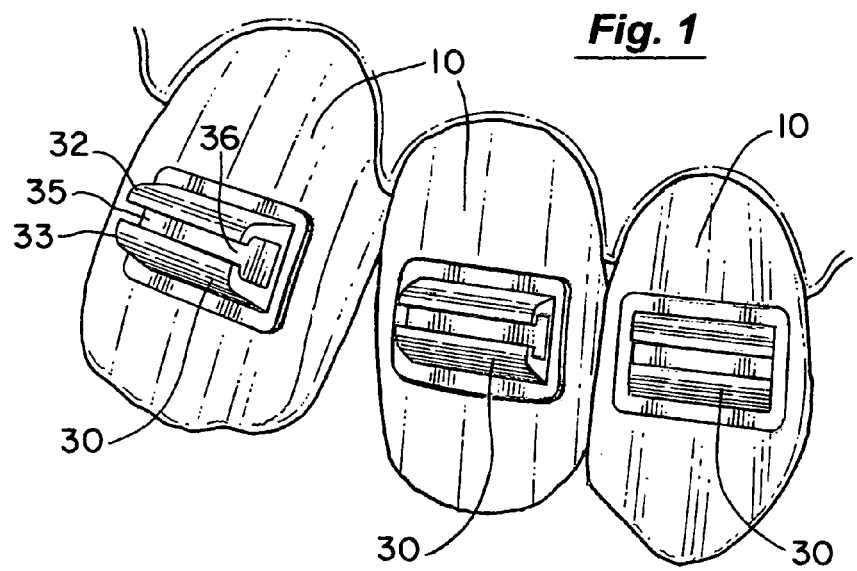
FIG. 1 is a front perspective view of a series of teeth 10 with orthodontic brackets 30 attached.

The present invention provides a novel two-part assembly consisting of a bracket 30 and an insertable clip 40. FIG. 1 provides a perspective view showing a series of teeth 10 with orthodontic brackets 30 attached. The bracket 30 has a gingival arm 32 and an occlusal arm 33 extending outward from the base 31 that together form a bracket slot 35 extending in a generally mesial-distal direction through the bracket 30. The arms 32, 33 of the bracket 30 extend at first in a labial or buccal direction outward, away from the base 31 of the bracket 30. While extending outward from the full mesial-distal width of the bracket 30, the arms 32, 33 thereafter curve generally inward toward each other providing a positive draft that narrows at points further from the tooth surface to form a neck 36 extending axially along at least portions of the bracket slot 35. The arms 32 and 33 shown in FIG. 1 extend the entire length of bracket slot 35. However, it should be understood that the arms 32, 33 could be designed to extend along only portions of the bracket slot 35. The bracket 30 can be made of any of a variety of materials, such as metal and alloys (e.g., stainless steel, titanium alloys), non-metals (e.g., glass, crystal, ceramics, or plastics), or composite materials (e.g., glass-reinforced polycarbonate).

The bracket slot 35 is dimensioned to receive a conventional orthodontic archwire 20. Similar to conventional brackets, the bracket slot 35 formed in the bracket 30 includes a floor of sorts that is oriented generally perpendicularly relative to the occlusal plane. The floor of the bracket slot 35 spans the width between the outward extending arms 32, 33. A functional relationship between the features of the present invention typically requires a floor width that is greater than the width of the neck 36 between the gingival and occlusal arms 32, 33. The lingual floor width is also typically greater than the width of the archwire 20. Additionally, the width of the neck 36 between the arms 32, 33 should be greater than the largest corresponding dimension of any archwire 20 to be received during treatment, so that an archwire 20 can be freely inserted through the neck 36 into the bracket slot 35.

The structure of the bracket 30 extending below the floor toward the tooth-contacting surface can be configured on a tooth-by-tooth basis. The bracket 30 is configured as required for the present innovative design to serve as a system of brackets for treating all of the teeth of an orthodontic patient. In such a system of brackets, each bracket is accommodative of known tooth morphology norms in terms of torque, prominence, rotation, angulation and right/left-handedness values, as well as tooth crown curvature values, specific to each of the twenty teeth typically involved in orthodontic correction.

Figure 2:
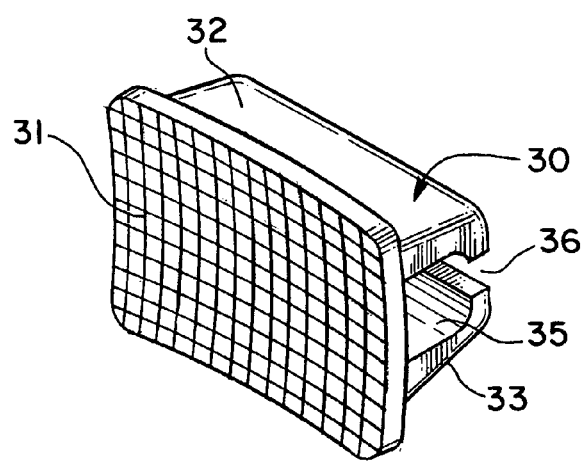
FIG. 2 is a rear perspective view of a bracket 30 showing its base 31.

Each bracket 30 for example will include a base 31 with a mounting portion for contacting a tooth 10. For example, FIG. 2 is a rear perspective view of a bracket 30 showing its base surface 31. This base 31 may be accommodative of a separate bonding pad. A bonding pad may consist of a fine stainless screen calendared to a thin stainless foil. Bonding pads are a well-known means of attaching orthodontic brackets to teeth using orthodontic adhesives. Bonding pads are typically attached to a bracket by brazing. As a bracket is bonded to a prepared tooth surface, the orthodontic adhesive mechanically registers into the fine screen creating a mechanical bond between it and the tooth.

The lingual-most surface 31 of the bracket 30 may alternatively exhibit mechanically retentive features integrally contained thereon. Such brackets are known as "one-piece" and during manufacture do not require the separate step of brazing a mesh bonding pad to the bracket. Integral bonding features of the type described can be understood by viewing U.S. Pat. Nos. 5,158,452 and 5,362,232 (Franseen et al.).

Alternatively, yet another means for attaching a bracket 30 to a tooth is to utilize brackets that have welding tabs or flanges. Such flanges are useful for resistance-welding a bracket to a tooth-encircling stainless steel band. Dental bands are formed of soft, malleable stainless steel and are generally anatomically shaped according to tooth morphology. Bands, and brackets attached thereto, are seated on teeth with cements formulated to immovably adhere bands. Whether a mesh pad is brazed on as a separate step or mechanically retentive features are incorporated integrally within the structure of the bracket, or a bracket is welded to a band, the configuration of the lingual most-surface of the bracket typically presents a compound, concave curved mounting surface. The surface must be generally accommodative of the statistically known curvature values of each of the teeth. Further, the relationship of the axis of the mesial-distal curvature and occlusal gingival curves need not be perpendicular to each other, reflecting known angulation values of human teeth. The apex of the radii need not fall on the geometric centerline of the lingual most surface of the bracket. The compound curvature may be biased to the mesial or distal to accommodate rotation values such as those specified by a popular bracket prescription known as the Roth prescription. Finally, the height above the tooth enamel that the bracket body floor is held is known as the prominence value. Some brackets will exhibit a low prominence value for those teeth that are naturally positioned more prominently such as the cuspids or upper centrals. Other brackets will have a low prominence value for those teeth that are naturally more inset such as maxillary laterals.

After the bracket 30 has been attached to its corresponding tooth 10, an archwire 20 is positioned in the patient's mouth and urged through the neck 36 of bracket arms 32, 33 and into the bracket slots 35 of all of the brackets 30. Alternatively, the archwire can be easily inserted in the axial direction for teeth located at the posterior ends of an arch. At that point, the relationship between the brackets 30 and the archwire 20 is non-precise and the archwire 20 is held only loosely in the brackets 30.

Figure 3:
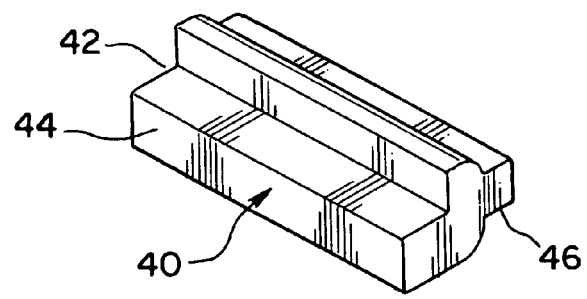
FIG. 3 is a perspective view of a clip 40.

In the embodiment depicted in FIGS. 1 and 2, the arms 32, 33 of the bracket 30 first extend perpendicularly away from the floor of the bracket, thus forming two 90° corners at the gingival and occlusal extent of the floor. The practitioner urges the archwire 20 into one or the other of these two corners. With the archwire 20 pushed into its corner, the lead-in end of a clip 40 is brought into axial alignment with an end of bracket slot 35 and the clip 40 is pushed partially into the bracket slot 35 of the bracket 30. FIG. 3 is a perspective view of a clip 40. The bracket 30 captures and removably retains the clip 40 within its structure as the clip is inserted in a mesial or distal direction into the end of the bracket slot 35 of the bracket 30. In other words, insertion of the clip 40 is accomplished in a generally horizontal direction along the axis of the archwire 20 and the bracket slot 35. Prior to insertion of the clip 40, there is space between the archwire 20 and walls of the bracket slot 35. As the clip 40 is inserted, this space is partly or fully filled with the clip 40, thereby forcing the archwire 20 to one corner of the bracket slot 35, as illustrated in FIG. 4, and thus engaging the archwire 20 to the bracket 30 for control. FIG. 5 is a perspective view corresponding to FIG. 1 showing a series of teeth 10 with brackets 30 after the archwire 20 and clips 40 have been inserted.

To fully understand the relationship of the system at this point, the reader should understand that in cross-section the clip 40 is shaped to intimately comply with the inner-facing surfaces of the bracket slot 35 (i.e., the floor, the adjacent perpendicular portions of the inner walls of the arms 32, 33, and narrowed neck 36). In particular, the cross-sections of the clip 40 and bracket slot 35 are designed to allow the clip 40 to slide into bracket slot 35 along the axis of the archwire 20. But, the narrowed neck 36 in the bracket slot 35 retains the clip 40 and prevents it from being readily withdrawn from the bracket slot 35 through the neck 36 in a labial or buccal direction. In the embodiment shown in FIG. 3, the clip 40 also exhibits a labial or buccal-most spine 46 that extends into the narrowed neck 36 formed between the labial or buccal-most extent of the bracket arms 32, 33. The spine 46 has locking features described below to removably secure the clip 40 in the bracket slot 35. The clip 40 can be made of any of a variety of materials or combinations of materials, such as plastic, ceramic, glass, crystal, metal, or composite materials.

The clip 40 can be equipped with a channel 42 extending the length of the clip 40 to receive an archwire 20. For example, as shown in FIG. 3, this channel 42 may extend axially along one of the lower (floor contacting) corners of the clip 40 to accommodate the archwire 20. In this embodiment, the channel 42 has two walls—one perpendicular and one parallel to the floor of the bracket slot 35. The base surface 44 of the clip 40 contacts the floor of the bracket slot 35 in the bracket 30, while the two channel walls in conjunction with the two walls associated with the bracket slot 35 (i.e., defined by the floor and arm corner of the bracket 30) combine to form a passageway for the archwire 20 through the assembly. In this manner, two walls of the bracket 30 and two walls of the clip 40 serve to completely capture all four surfaces of an archwire 20 having a conventional rectangular cross-section.

As previously described, during the process of capturing of an archwire 20 into the bracket slots 35, an archwire 20 is urged in position through the neck 36 and into the bracket slots 35 of all of the brackets 30 bonded to the teeth of an upper or lower dental arch. Preferably, each clip 40 exhibits a tapered end, which is inserted first into the bracket slot 35 in its corresponding bracket 30. One by one, the clips are inserted into the brackets by first aligning each clip 40 with the archwire 20 and bracket slot 35, and then carefully sliding the clip 40 along the archwire 20 into the bracket slot 35 (i.e., along a mesial-distal axis) between the arms 32 and 33, so that archwire 20 is held between the clip 40 and the bracket 30.

It should be noted that the clip 40 can be inserted either with the channel 42 up or down in the embodiment depicted in FIGS. 1 and 2. This allows the practitioner to select which corner of the bracket slot 35 will hold the archwire 20. This feature can be useful in exerting a therapeutic force in the gingival/occlusal axis to accentuate leveling of the teeth 10.

Optionally, after the clip 40 has been partially inserted into a bracket 30, any one of several standard orthodontic instruments (e.g., pliers) can be used to fully insert the clip 40 into the bracket slot 35 of the bracket 30. For this, one beak of a pliers can contact a distal edge of a bracket 30 while the other beak can contact the mesial end of the clip 40. Moderate squeezing of the pliers will push the clip 40 fully into position. Importantly, as the clip 40 is pliered into position in this manner, the relative moments of torsion and bending are cancelled out within the structural system consisting of the bracket 30, the archwire 20, and the clip 40.

The clip 40 shown in FIG. 3 includes a spine 46 that fills the narrowed neck 36 between the labial or buccal-most portions of the arms 32, 33 of the bracket shown in FIG. 2. A cross-sectional view of the resulting assembly of the clip 40 and bracket 30 is depicted in FIG. 4. The labial or buccal-most portions of the arms 32, 33 exhibit inward-facing parallel faces that matingly contact the gingival and occlusal surfaces of the clip's spine 46. Friction between the clip 40, archwire 20, and bracket 30 will tend to keep the clip 40 in place in the bracket slot 35. However, the clip 40 can also be held in place in the bracket slot 35 by means of a locking mechanism that can further restrict axial movement of the clip 40 in the bracket slot 35 (e.g., at least one set of complementary protrusions 48 and indentations 38). In the embodiment shown in FIG. 17, the occlusal and gingival surfaces of the spine 46 of the clip 40 exhibit a raised protrusion 48 that may be centered or slightly off-center along its mesial-distal extent. As the clip 40 reaches its fully inserted position within the bracket slot, the protrusion 48 falls into registration with a corresponding indentation 38 in the inward-facing parallel faces at the buccal or labial-most extent of the arms 32, 33 of the orthodontic bracket 30. As the protrusion 48 and indentation 38 fall into registration, a slight resiliency or spring property of the arms 32, 33 causes the clip 40 to positively snap into a locked and immobilized relation with the bracket slot (i.e., a snap fit). Alternatively, a friction fit could be use to removably secure the protrusion 48 and indentation 38 in registration with one another. The relationship of this locking mechanism provides a positive means of removably securing the assembly and preventing undesirable sliding movement or loss of the clip 40 relative to the bracket 30 during treatment.

Figure 17:
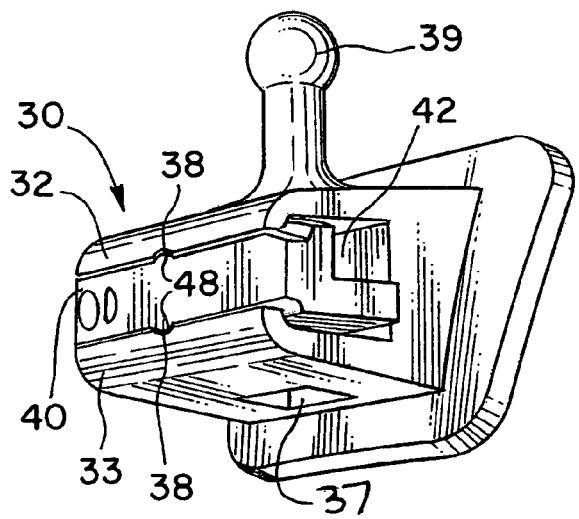
FIG. 17 is a perspective view of a bracket 30 including a rhomboid bonding pad in a torqued relation to the bracket slot, a hook 39, and a vertical slot 37, as well as clip retention features including a clip 40 with indentations 38 and protrusions 48 to retain the clip 40 in the bracket slot of the bracket 30.

As described previously, the protrusion 48 and indentation 38 can be centered or located slightly off-center relative to the full mesial-distal extent of the clip 40, as can be seen in FIG. 17. And as also described previously, one end of the clip 40 can be tapered to permit easier initial insertion of the clip 40 into the bracket slot. Optionally, the relationship between the length of the bracket 30, the length of the clip 40 and the positioning of the protrusion 48 and indentation 38 may combine to allow the tapered portion of the clip 40 to extend out beyond the end of the bracket 30 when the protrusion 48 and indentation 38 are in locking registration, as shown in FIG. 17. In addition, optional visual indicia (e.g., markings or color coding) can be incorporated into the clip 40, as also shown in FIG. 17, so that the practitioner can readily identify the appropriate type of clip to use with each bracket.

Just as pliers can be used to fully move the clip 40 mesially or distally into a fully locked position relative to the bracket, pliering can also be employed to unseat and remove the clip 40. For example, one beak of a pliers can rest against the mesial end of the bracket 30 while the other beak is in contact with the end of the distal-extending tapered portion of the clip 40 that extends distally out of a bracket 30. Moderate squeezing of the pliers will cause the tapered end of the clip 40 to be pushed mesially until the distal end of the clip 40 is flush with the distal end of the bracket 30. The amount of relative movement of the clip 40 from its initial locked position to a position where in this example the distal end of the clip 40 is flush with the distal end of the bracket 30 is intended to be the amount of relative movement required to disengage the locking mechanism. Once the protrusion 48 and indentation 38 are no longer in registration, the clip 40 can be grasped with the dental pliers and fully removed from the bracket slot 35, allowing the archwire 20 to be removed through the neck 36 of the bracket slot 35.

Figure 18:
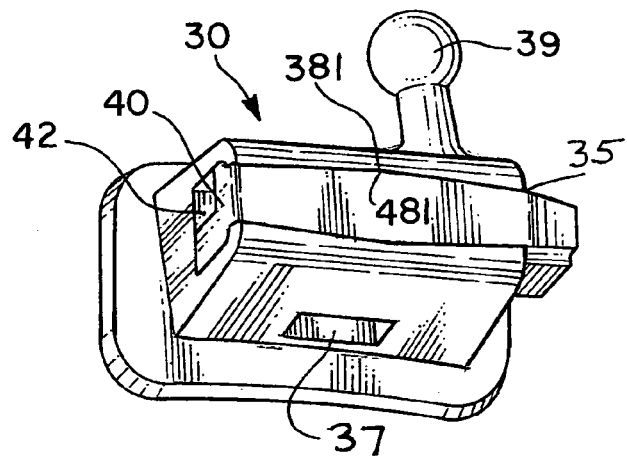
FIG. 18 is a perspective view of an embodiment of the clip 40 and bracket 30 that includes complementary profiled walls 381, 481 to form a locking mechanism to retain the clip 40 in the bracket slot 35.

FIG. 17 shows an embodiment in which the single small rounded protrusion 48 extends from the clip 40 to engage a complementary rounded indentation 38 in the neck of the bracket slot. The shape and size of the indentation 38 and protrusion 48 are largely a matter of design choice. It should also be expressly understood that the relative positions of the indentation 38 and protrusion 48 can be reversed, and that any number of sets of indentations and protrusions could be used. FIG. 18 illustrates an another embodiment in which the protrusion is a long profiled wall 481 in the clip 40, and the indentation is a corresponding profiled wall 381 in the bracket slot 35, rather than the sharp protrusion/intent previously described. The terms "protrusion" and "indentation" should also be broadly interpreted to cover any type of locking mechanism to restrict axial movement of the clip in the bracket slot and thereby removably retain the clip 40 in the bracket slot. In addition, the term "locking mechanism" should be broadly interpreted to cover any mechanism for removably securing the clip 40 to the bracket slot 35. Possible alternatives include other types of latches, locks, clasps, pins, and one-time locking devices that are damaged or break on removal.

As can also be appreciated, the relative mesial distal length of the orthodontic bracket assembly can be varied according to treatment objectives and varied according to the teeth it is to be attached to. Generally, for brackets 30 of a reduced mesial-distal length, a correspondingly greater inter-bracket segment of the archwire 20 is created. Greater inter-bracket distance may lessen the physiologically effective forces delivered by a bracket system and as such, patient comfort is usually enhanced, or alternatively, increase the size of the deflection before the wire's elastic limit is reached. Conversely, longer bracket assemblies tend to reduce inter-bracket distance thereby concentrating strain in the resulting shorter archwire segment between the brackets, which tends to increase forces.

As previously described, conventional orthodontic brackets usually receive a sequential series of archwires as orthodontic treatment progresses. Most of those archwires are not full-sized wires because during earlier stages of treatment it may be desirable to have some "slop" between the bracket slot and the archwire due to the significantly out-of-alignment condition of the teeth. Otherwise, unacceptably high physiological forces could result in patient discomfort, along with injury to the roots of the teeth. The present invention accommodates the need for slop during the early phases of treatment by providing a clip that does not necessarily tightly capture the archwire. For example, if a 0.016×0.016 in. square arch wire is first being inserted, an orthodontist may opt to use a clip with an archwire-contacting profile larger than 0.016×0.016 inches. This allows the archwire some leeway and reduces the physiological forces delivered to a tooth and its supporting bone. At the next patient appointment, after the teeth have responded and moved closer to ideal positions, the clip may be replaced with a clip that more intimately captures the archwire within the bracket slot. Conversely, the latitude provided by being able to use clips of varying archwire-contacting dimensions allows smaller wires to be fully captured. For example, as above, a popular intermediate archwire size is 0.016 in. square. The present invention permits the use of an optional clip capable of fully capturing an 0.016 in. square archwire within the bracket if desired and later in treatment fully capturing a 0.018×0.025 in. archwire. In contrast, a conventional orthodontic bracket would be able to fully capture only one size archwire that exhibits full slot-filling dimensions.

The channel 42 in the clip 40 shown in FIG. 3 is intended to allow a standard archwire 20 to pass through, but without any slop. Its configuration can be manufactured to specifications whereby it desirably increases friction with the archwire to help hold a tooth in a desired position. Conversely, dimensions can be opened up to allow relative translation between the bracket and the archwire while maintaining full control of the tooth. For example, FIG. 6 illustrates an embodiment of the clip 40 having a curved channel 42 to accommodate curvature in the archwire 20. If the radius of curvature of the channel 42 is about the same as the anterior radius of an archwire (e.g., 0.625 in.), it can still be considered a no-slop engagement in that the channel 42 just accommodates the curvature of the archwire. Alternatively, the channel 42 can be made undersized to frictionally bind the archwire and prevent it from sliding.

Orthodontic bracket design and treatment philosophies of the past have required a variety of archwire sizes and shapes. The "twin arch" technique and "ribbon arch" technique are both examples of methods popularly used by orthodontists during the first half of the 1900's. Like modern approaches, these techniques called for archwires of standardized maximum dimensions just as current standards define a full size arch wire as being 0.018×0.025 in. for 0.018-slotted brackets and 0.022×0.028 in. for 0.022 slotted brackets. Unlike conventional brackets, the present invention is not limited to set maximum standards. The present invention, through the use of accordingly-configured clips is capable of accommodating archwires that are larger than the largest commercially available standard sizes and further, unlike conventional brackets, brackets and clip combinations of the present novel design can accommodate larger than standard or even one-of-a-kind archwires or multiple archwires that may be custom-fabricated for the needs of a particular extraordinary orthodontic case.

Again, FIG. 6 shows a clip relieved to neutrally accommodate a curved portion of an archwire. One set of standards for the radius of the anterior curvature of the human dentition, at least at the level that an archwire is normally positioned calls for a radius of 0.750 in. for the upper arch and 0.625 in. for the lower. FIG. 6 represents a relieved clip capable of exactly accommodating such known and standard curvatures. The apex of the relieved curvature in the clip, relative to the mesial and distal ends of the clip defines a height (H) corresponding to a 0.750 in. radius standard established for the upper arch for example. The present invention however anticipates a clip where the value of (H) is decreased. Such a clip of the present invention would tend to forcibly flatten and reduce the curvature of the section of archwire within the confines of the bracket. The flattening force of such as clip, once inserted, would tend to reduce H thus increasing the radius of the curvature locally, at least for that portion of the archwire contained within the bracket. A series of such anterior brackets however acting together to increase the entire anterior radius in this manner can collectively cause the archwire to respond as if it were in fact formed to have a larger anterior radius. In orthodontic terms, an archwire imparting such forces is called an "expansion arch." Expansion arches serve to bodily move teeth outward, eliminating crowding by defining larger anterior radius with sufficient arch length allowing the teeth to move into desirable inclinations without interfering or overlapping each other. The present invention is capable of taking a standard archwire with a neutral anterior radius and through the insertion of clips configured with a reduced H value, cause a standard archwire to act as an expansion arch.

Figure 7:
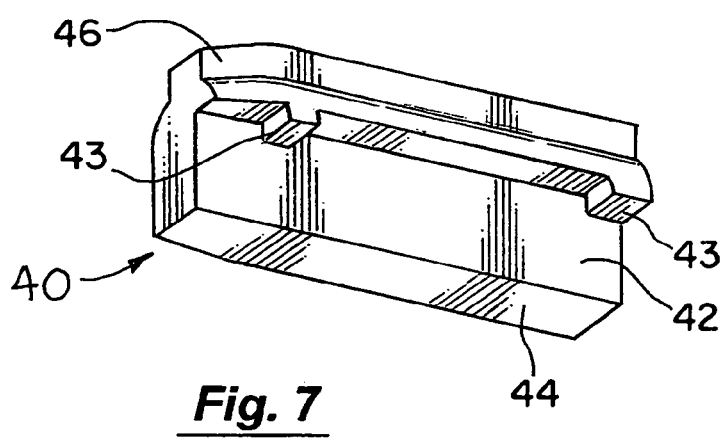
FIG. 7 is a perspective view of another embodiment of the clip 40 with contacts 43 in the channel 42 to accommodate either straight or curved segments of the archwire.

The clip depicted in FIG. 7 has a channel 42 with contacts 43 that accommodate straight segments of the archwire as well as curved. Further, the contacts 43 could be curved or rounded to reduce contact with the archwire 20.

Figure 8:
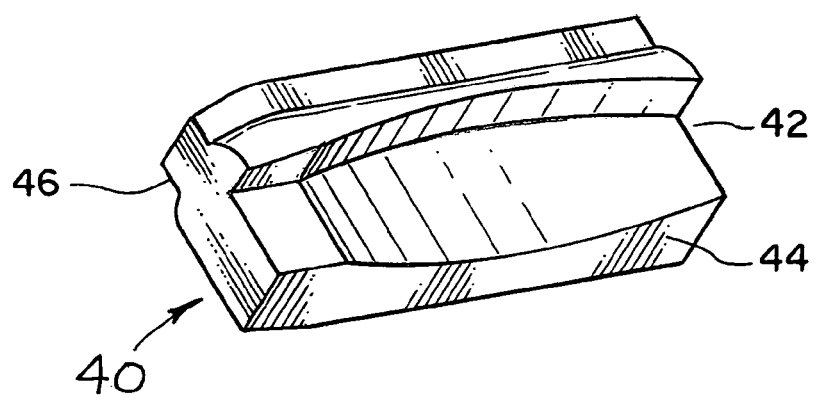
FIG. 8 is a perspective view of another embodiment of the clip 40 with a channel 42 that is curved in two orthogonal directions.
Figure 9:
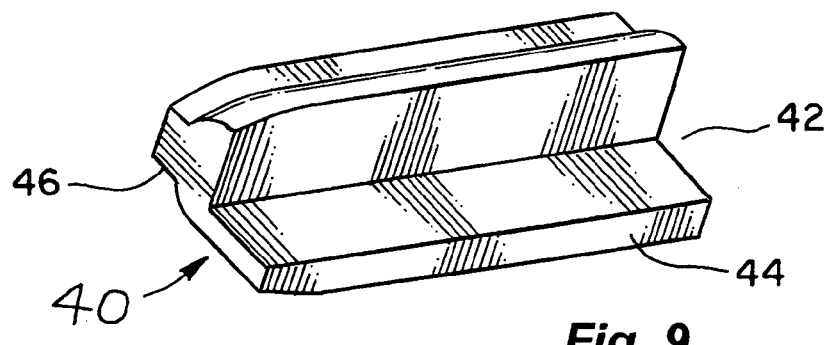
FIG. 9 is a perspective view of another embodiment of the clip 40 having a channel 42 shaped to allow tipping of a tooth or second order movement while maintaining tight control of the tooth in terms of rotation.
Figure 10:
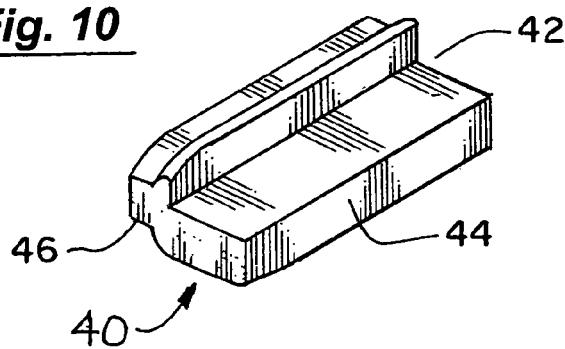
FIG. 10 is a perspective view of another embodiment of the clip 40 having a thinner buccal or labial wall, which provides a channel 42 shaped to allow significant rotation or first order movement of a tooth while providing tight control in terms of tip and some control in terms of torque.
Figure 11:
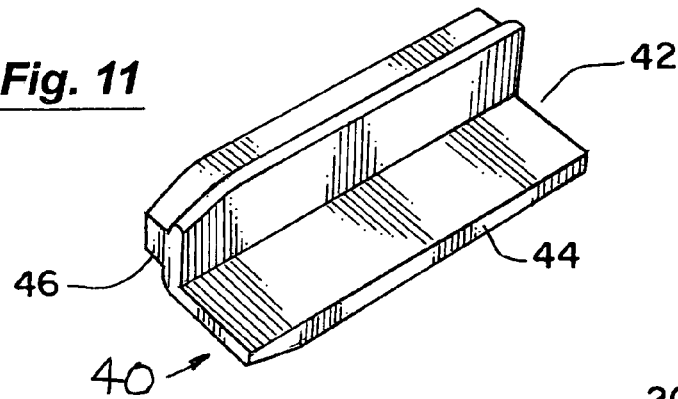
FIG. 11 is a perspective view of another embodiment of the clip 40 having a channel shaped to permit considerable slop between the archwire and bracket affording a degree of freedom about all axes.

The embodiment of the clip 40 shown in FIG. 8 permits curvatures in both labial-lingual and occlusal-gingival directions as is typically needed during earlier phases of treatment. The clip 40 illustrated in FIG. 9 allows second order or free tipping of a tooth in a clockwise or counter-clockwise direction while maintaining tight control of the tooth in terms of rotation and some control of torque. The embodiment of the clip 40 shown in FIG. 10 allows significant first order rotation of a tooth around the long axis, while providing some control in terms of torque and good control of second order movement (i.e., tipping). The embodiment of the clip 40 shown in FIG. 11 permits considerable slop between the archwire 20 and the bracket 30 affording a degree of freedom in all axes. This would allow what is known as first, second and third order freedom between the archwire and the tooth.

As can be appreciated, conventional brackets have a fixed-size bracket slot and have only a limited number of ways to engage an archwire. Brackets of the present invention introduce new ways of desirably directing, controlling or limiting the relative freedom of movement between an archwire and a bracket. In contrast to conventional brackets, the present invention provides increased options for archwire control and provides for enhanced sequential control of less than full size archwires. The design can be greatly reduced in size, compared to conventional orthodontic brackets particularly in the occlusal-gingival axis. The bracket design in the present invention does not require features that can undesirably create bacterial harbours that in turn can cause decalcification of the enamel and corrosion of the orthodontic hardware. Compared to conventional orthodontic brackets, the outward profile of the present invention is of a more rounded shape. All of these features lead to increased tolerance by patients due to less soft tissue irritation and a more aesthetic appearance.

Figure 12:
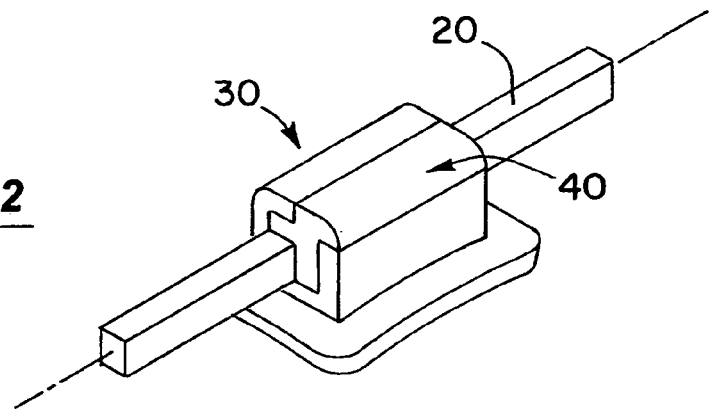
FIG. 12 is a perspective view of another embodiment of the bracket 30 and clip 40.
Figure 13:
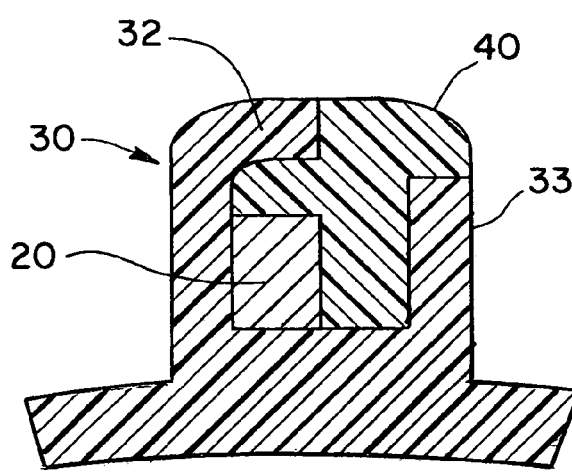
FIG. 13 is cross-sectional view of the embodiment of the bracket 30 and clip 40 shown in FIG. 12.

The degree to which the occlusal and gingival arms 32 and 33 of the bracket 30 are symmetrical or asymmetrical is largely a matter of design choice. For example, FIG. 12 is a perspective view of an embodiment of the bracket 30 and clip 40 with arms 32, 33 that are more asymmetrical than the previously-discussed embodiment. FIG. 13 is a corresponding cross-sectional view. This embodiment allows the archwire 20 to be tucked into the corner of the bracket slot 35 immediately under the curved arm 32 to provide structural support to help prevent the clip 40 from being pulled out of the bracket slot by labially-directed forces carried by the archwire 20. Depending on location, either arm 32 or 33 can be the arm that is curved. Such a configuration also provides the combined structural support of both the clip and the bracket, reducing the potential for forces carried by the archwire to distort the bracket structure, which could result in mechanical failure of the assembly. It should be understood that other configurations of the bracket slot 35 and clip channel 42 are possible, so that the archwire 20 is contained between the clip 40 and the walls of the bracket slot 35. In essence, the bracket slot 35 and clip channel 42 together form an archwire slot to contain the archwire 20. If the clip is camouflaged or colored (e.g., to match tooth color), this compact bracket/clip combination will also aesthetically hide much of the bracket 30.

Figure 14:
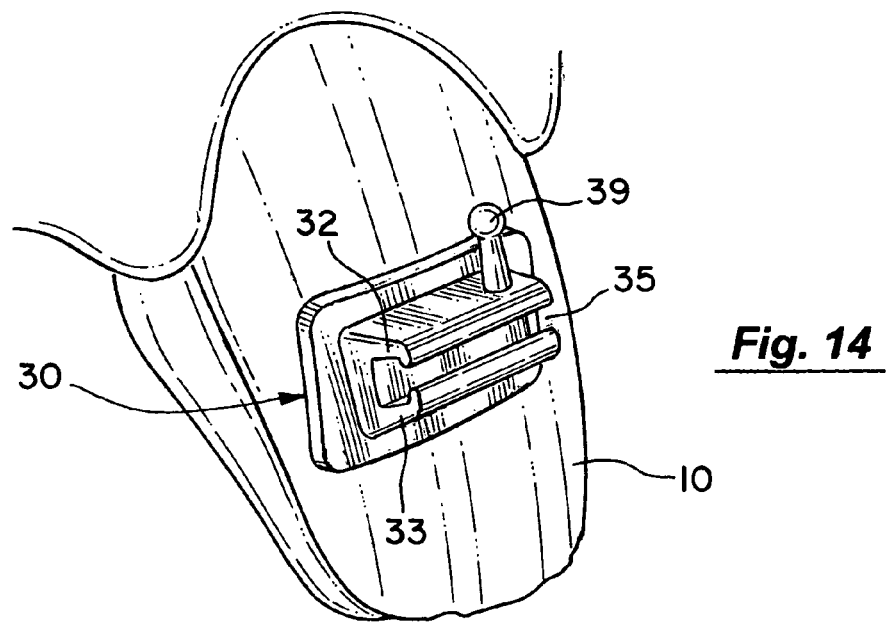
FIG. 14 is a perspective view of an embodiment of the bracket 30 having a bonding pad mounted on a tooth 10.

FIG. 14 is a perspective view of an embodiment of the bracket having a bonding pad mounted on a tooth 10. The right and left edges of the pad are generally parallel to the mesial and distal edges of the tooth 10. The top and bottom edge of the pad are generally parallel to the incisal edge of the tooth, or at least parallel to the occlusal plane at the end of treatment. Brackets and their bonding pads can be readily produced in a variety of sizes and contours and auxiliary features as a system to accommodate all of the teeth to be bracketed during orthodontic treatment.

Figure 15:
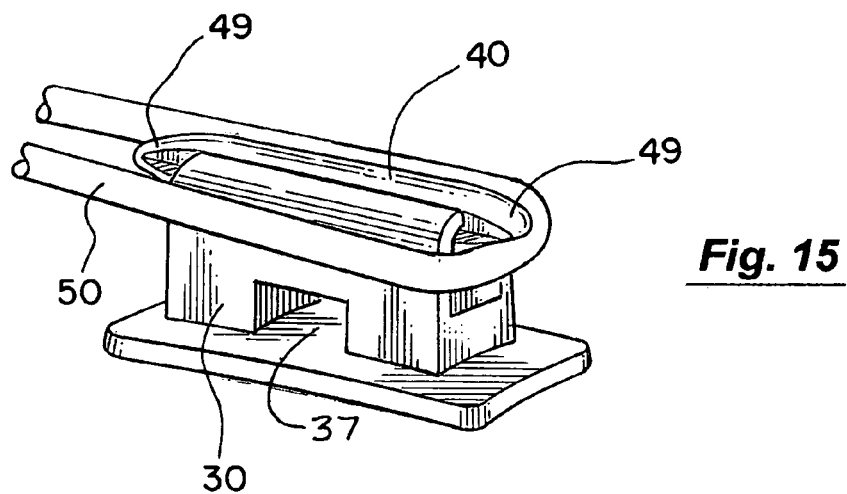
FIG. 15 is a perspective view of an embodiment of the clip 40 and bracket 30, in which the end of the clip 40 includes a nose or projection 49 to engage an elastic 50.
Figure 16:
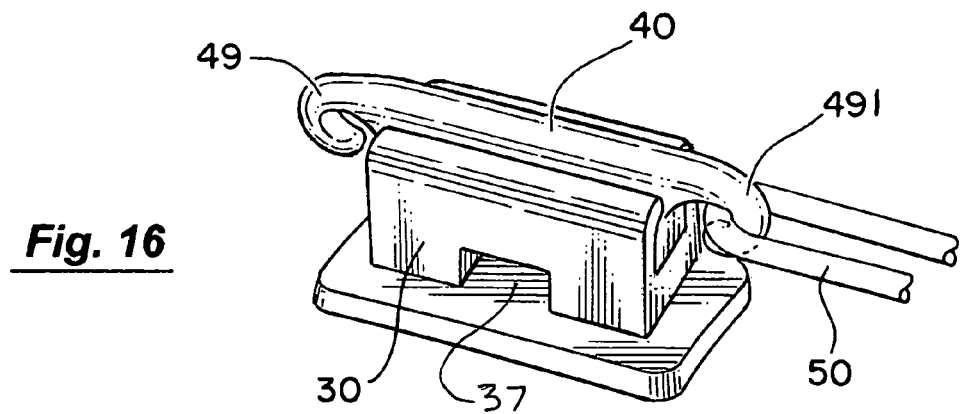
FIG. 16 is a perspective view of an embodiment of the clip 40 and bracket 30, in which the ends of the clip 40 form hooks 491 to engage an elastic 50.

Optionally, either the bracket 30 or clip 40 can be equipped with protrusions or hooks to allow attachment of elastics, traction springs, or other conventional devices to exert a therapeutic force between teeth or groups of teeth. FIGS. 14, 17 and 18 show examples of such a protrusion or projection 39 extending from the bracket 30. FIG. 15 is a perspective view of an embodiment in which the end of the clip 40 includes a nose or projection 49 extending beyond the bracket slot 35 to engage an elastic 50. If desired, projections 49 can be formed at both ends of the clip 40. FIG. 16 is a perspective view of an embodiment of the clip 40 and bracket 30, in which the ends of the clip 40 form hooks 491 to engage an elastic 50. This embodiment of the bracket 30 also includes a vertical slot 37 to allow other types of conventional orthodontic attachments. The bracket shown is representative of a fully pre-programmed bracket embodying angulation, torque, prominence, and other useful features such as a vertical slot 37 and an elastic hook. Such a bracket should be considered integral to a system of brackets, each bracket tailored to accommodate the morphology of a specific tooth and the system configured to treat one patient.

Figure 20:
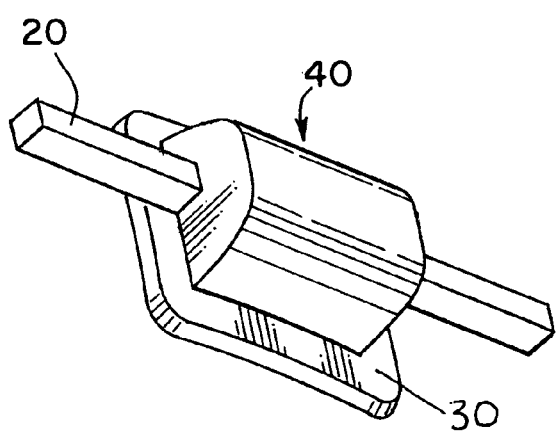
FIG. 20 is a top perspective view of the embodiment of the clip 40 shown in FIG. 19 after it has been inserted over a bracket 30 and archwire 20.
Figure 19:
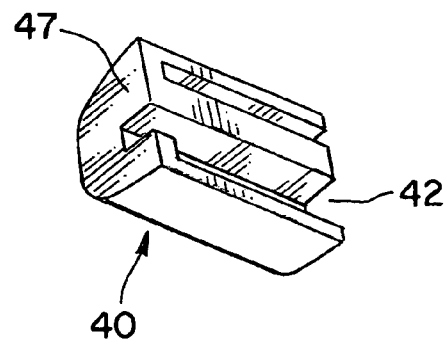
FIG. 19 is a bottom perspective view of another embodiment of the clip 40 having an end cap 47 that limits insertion of the clip 40 into the bracket beyond a predetermined point.

FIG. 19 is a bottom perspective view of an embodiment of the clip 40 having an end cap 47 that prevents insertion of the clip 40 into the bracket beyond a predetermined limit. FIG. 20 is a top perspective view of the embodiment of the clip 40 shown in FIG. 19 after it has been inserted over a bracket 30 and archwire 20.

FIGS. 21 and 22 illustrate another embodiment of the invention in which the clip 40 includes a bracket-camouflaging or decorative cap 45 atop the tapered spine 46 that covers portions of the exterior surfaces of the bracket arms 32, 33. This embodiment of the clip 40 also includes large barbell-shaped projections 492 to fasten elastics to the clip 40. FIG. 23 extends the concept of a cap 45 to the point of almost covering the exterior of the bracket arms 32, 33 with a projection 493 extending from either the gingival or occlusal surface of the cap 45.

The above disclosure sets forth a number of embodiments of the present invention. Other arrangements or embodiments, not precisely set forth, could be practiced under the teachings of the present invention and as set forth in the following claims.

I claim:

1. An orthodontic bracket assembly for removably securing an archwire of substantially rectangular cross-section to a patient's tooth, said orthodontic bracket assembly comprising:
    a bracket having:
        (a) a base with a mounting portion for attachment to a patient's tooth; and
        (b) a plurality of arms forming a bracket slot to receive an archwire; and
    a clip removably insertable into the bracket slot along the axis of the bracket slot and archwire, and being retained by the bracket slot to removably secure an archwire in the bracket slot, with two surfaces of the archwire being engaged by the bracket and the remaining two surfaces of the archwire being engaged by the clip.

2. The orthodontic bracket assembly of claim 1 further comprising a locking mechanism to restrict axial movement of the clip in the bracket slot.

3. The orthodontic bracket assembly of claim 2 wherein the locking mechanism comprises at least one complementary set of indentations and protrusions on the clip and bracket slot to restrict axial movement of the clip in the bracket slot.

4. The orthodontic bracket assembly of claim 1 wherein the arms form a narrowed neck in the bracket slot to retain the clip in the bracket slot.

5. The orthodontic bracket assembly of claim 1 wherein the clip further comprises a projection extending beyond the bracket slot.

6. The orthodontic bracket assembly of claim 1 wherein the clip further comprises a channel extending the length of the clip to receive an archwire.

7. The orthodontic bracket assembly of claim 1 wherein the bracket slot has a lingual floor with a width greater than the width of the archwire.

8. An orthodontic bracket assembly for removably securing an archwire of substantially rectangular cross-section to a patient's tooth, said orthodontic bracket assembly comprising:
    a bracket having:
        (a) a base with a mounting portion for attachment to a patient's tooth; and
        (b) a plurality of arms forming a bracket slot extending along a generally mesial-distal axis, with at least portions of the bracket slot having a narrowed neck allowing an archwire to be inserted into the bracket slot; and
    a clip removably insertable into the bracket slot along the axis of the bracket slot and archwire, and being retained by the neck of the bracket slot to removably secure an archwire in the bracket slot, with two surfaces of the archwire being engaged by the bracket and the remaining two surfaces of the archwire being engaged by the clip.

9. The orthodontic bracket assembly of claim 8 further comprising a locking mechanism to restrict axial movement of the clip in the bracket slot.

10. The orthodontic bracket assembly of claim 9 wherein the locking mechanism comprises at least one complementary set of indentations and protrusions on the clip and bracket slot to restrict axial movement of the clip in the bracket slot.

11. The orthodontic bracket assembly of claim 8 wherein the clip further comprises a projection extending beyond the bracket slot.

12. The orthodontic bracket assembly of claim 8 wherein the clip further comprises a channel extending the length of the clip to receive an archwire.

13. The orthodontic bracket assembly of claim 8 wherein the bracket slot has a lingual floor with a width greater than the width of the archwire.

14. An orthodontic bracket assembly for removably securing an archwire of substantially rectangular cross-section to a patient's tooth, said orthodontic bracket assembly comprising:
a bracket having:
(a) a base with a mounting portion for attachment to a patient's tooth; and
(b) a plurality of arms forming a bracket slot extending along a generally mesial-distal axis to receive an archwire; and a clip removably insertable into the bracket slot along the axis of the bracket slot and archwire, and having a channel extending along the length of the clip, whereby insertion of the clip into the bracket slot removably secures the archwire in the channel of the clip and the bracket slot, with two surfaces of the archwire being engaged by the bracket and the remaining two surfaces of the archwire being engaged by the clip.

15. The orthodontic bracket assembly of claim 14 wherein the arms form a narrowed neck extending along at least portions of the bracket slot to retain the clip in the bracket slot.

16. The orthodontic bracket assembly of claim 14 further comprising a locking mechanism to restrict axial movement of the clip in the bracket slot.

17. The orthodontic bracket assembly of claim 16 wherein the locking mechanism comprises at least one complementary set of indentations and protrusions on the clip and bracket slot to restrict axial movement of the clip in the bracket slot.

18. The orthodontic bracket assembly of claim 14 wherein the clip further comprises a projection extending beyond the bracket slot.

\* \* \* \* \*